United States Patent [19]

Ishiguro et al.

[11] Patent Number: 5,131,396
[45] Date of Patent: Jul. 21, 1992

[54] ULTRASONIC INTERNAL EXAMINATION SYSTEM

[75] Inventors: Masaaki Ishiguro; Toshizumi Tanaka; Yukio Takagi, all of Omiya, Japan

[73] Assignee: Fuji Photo Optical Co., Ltd., Omiya, Japan

[21] Appl. No.: 718,642

[22] Filed: Jun. 21, 1991

[30] Foreign Application Priority Data

Jun. 25, 1990 [JP] Japan ................................ 2-164247

[51] Int. Cl.⁵ .............................................. A61B 8/14
[52] U.S. Cl. ........................... 128/662.03; 128/662.06; 128/660.1
[58] Field of Search ...................... 128/660.01, 660.09, 128/660.1, 662.03, 662.06

[56] References Cited

U.S. PATENT DOCUMENTS

| | | | |
|---|---|---|---|
| 4,432,371 | 2/1984 | McAusland | 128/660.1 |
| 4,494,549 | 1/1985 | Namba et al. | 128/662.06 |
| 4,757,819 | 7/1988 | Yokoi et al. | 128/662.06 |
| 4,911,170 | 3/1990 | Thomas, III et al. | 128/662.06 |
| 4,911,173 | 3/1990 | Terwilliger | 128/662.06 |

Primary Examiner—Francis Jaworski
Assistant Examiner—George Manuel
Attorney, Agent, or Firm—Oblon, Spivak, McClelland, Maier & Neustadt

[57] ABSTRACT

Described herein is an ultrasonic internal examination system of the type having a rigid tip portion at the distal end of an ultrasonic probe to be inserted into an intracavitary portion of interest, and an ultrasonic vibratory element accommodated in a cavity formed in the rigid tip portion and filled with an ultrasonic transmissive medium for transmission and reception of signals. The rigid tip portion is formed with a cylindrical shaped outer configuration and internally defines a cavity having a radially concave curved inner wall surface of a predetermined radius of curvature on the inner periphery thereof.

2 Claims, 7 Drawing Sheets

FIG. 6
FIG. 7
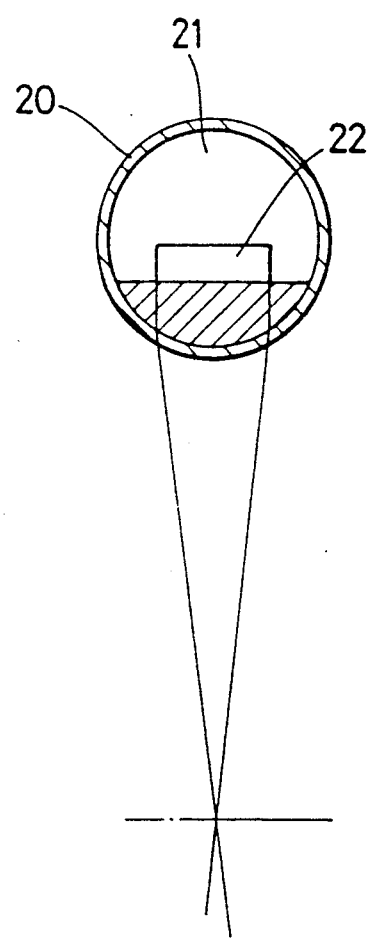
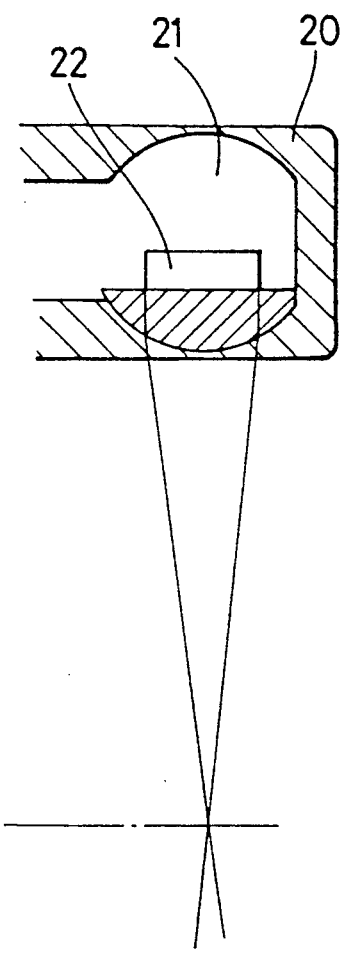

ULTRASONIC INTERNAL EXAMINATION SYSTEM

FIELD OF THE ART

This invention relates to an ultrasonic internal examination system having an ultrasonic probe to be inserted into an intracavitary portion of a human body or the like for examination of intracorporeal tissues of interest.

BACKGROUND OF THE ART

In ultrasonic internal examination, for example, in case of radial scan type ultrasonic internal examination using mechanical radial scanning, an ultrasonic vibratory element is usually accommodated in a casing which contains an ultrasonic transmissive medium in a sealed state. As the ultrasonic vibratory element is turned manually or mechanically through a drive means, ultrasonic energy is directed into an intracavitary wall of interest while receiving return echo signals from the wall tissues and processing the received signals at an ultrasonic image observation terminal to display on a monitor an ultrasonic image which gives information concerning a cross-sectional area of the wall tissues.

In order to improve the picture quality of the above-mentioned sectional ultrasonic image, it is necessary to narrow the ultrasonic beam to be directed into a body. This can be achieved to a certain extent, for example, by employing an aperture of suitable construction for the ultrasonic vibratory element. However, it is difficult to converge the ultrasonic beam to a necessary degree simply through revision of the aperture construction of the ultrasonic vibratory member, which requires troublesome machining operations and would result in a very expensive ultrasonic vibratory element.

In this connection, there has been developed an ultrasonic probe construction, in which the ultrasonic transmissive medium sealed in the casing of the vibratory element is used as an acoustic lens based on the difference in acoustic impedance of the ultrasonic transmissive medium from the casing and intracavitary wall tissues to be examined.

In utilizing the ultrasonic transmissive medium in the casing as an acoustic lens as mentioned above, it may be conceivable to employ a casing of hollow spherical shape for the ultrasonic vibratory element. However, a problem which arises in the fabrication of casings of such a hollow spherical shape is that the machining of the inner wall surfaces is extremely difficult. Besides, if incorporated into an ultrasonic probe to be inserted into human body for ultrasonic examination, the tip end of the probe would be bulged out in spherical shape, making it difficult to insert the probe into a narrow or constricted intracavitary portion and at the same time degrading the operationability of the probe, for example, by increasing the resistance to the efforts of withdrawal.

In case of an endoscope, typical of the instruments widely used for internal examination and diagnosis, its insert portion is normally of a cylindrical shape having a uniform diameter substantially over the entire length thereof. This shape has been selected in consideration of various conditions including operability at the time of insertion etc. For instance, the fore end of the insert portion is formed so as to have a smooth and uniform outer configuration almost free of surface irregularities to ensure smooth passage through constricted portions which might exist in the path of insertion of the endoscope. The ultrasonic internal examination system, which is designed to be inserted into a human body similarly to the endoscope, is preferred to have an insert portion of a cylindrical shape having a uniform diameter substantially over its entire length. In addition, a spherically shaped tip end is disadvantageous in consideration of the necessity for fitting a balloon at the tip end of the insert portion for the purpose of standoff, which is required by the ultrasonic examination system itself. Further, in a case where the ultrasonic examination system is used as an ultrasonic endoscope which combines the functions of the endoscope with an ultrasonic examination system, a bulged portion at the tip end of the ultrasonic probe should be avoided from the standpoint of securing a sufficient field of view and preventing reflections of illuminating light.

For the reasons stated above, existing ultrasonic internal examination systems of the type to be inserted into an intracavitary or other internal portion invariably have an ultrasonic vibratory element accommodated in a cylindrical rigid tip portion. An ultrasonic probe with such a cylindrical tip end has a circular shape in section in a direction perpendicular to its axis and thus could be arranged to have the function of acoustic lens in the axial direction. On the other hand, it has a flat shape in section in the axial or longitudinal direction, which practically would not lead to any useful lens effects. Namely, a radial ultrasonic beam pattern directed from the ultrasonic vibratory element can only be converged into an undesirably flattened elliptical shape.

SUMMARY OF THE INVENTION

It is therefore an object of the present invention to provide an ultrasonic internal examination system which employs a rigid tip of a cylindrical outer configuration at the distal end of an ultrasonic probe, and yet which is capable of converging a radial ultrasonic beam into a desired condition.

In accordance with the present invention, there is provided, for achieving the above-stated objective, an ultrasonic internal examination system of the type having a rigid tip portion at the distal end of an ultrasonic probe to be inserted into an intracavitary portion of interest, and an ultrasonic vibratory element accommodated in a cavity formed within the rigid tip portion and filled with an ultrasonic transmissive medium for transmission and reception of ultrasonic signals, characterized in that the rigid tip portion is formed of a cylindrical shape in outer configuration and internally defines a cavity having a radially concave curved inner wall surface of a predetermined radius of curvature on the inner periphery thereof.

BRIEF DESCRIPTION OF THE DRAWINGS

The above and other objects, features and advantages of the invention will become apparent from the following description and the appended claims, taken in conjunction with the accompanying drawings which show by way of example preferred embodiments of the invention. Needless to say, the invention is not restricted to the particular forms shown in the drawings, in which:

FIGS. 1 through 6 show a first preferred embodiment of the invention, of which:

FIG. 1 is a schematic view of an ultrasonic endoscope as a whole;

FIG. 2 is a schematic sectional view of a distal end portion of an ultrasonic probe;

FIG. 3 is a schematic sectional view of an ultrasonic probe operating mechanism;

FIG. 4(a) is a schematic perspective view of a rotating mechanism for the ultrasonic vibratory member;

FIG. 4(b) is a view explanatory of the operation of the rotating mechanism;

FIG. 5 is a schematic sectional view of a rotary connector;

FIGS. 6 and 7 are sectional views taken on lines VI—VI and VII—VII of FIG. 2, respectively, showing the ultrasonic vibratory member and its beam pattern.

DESCRIPTION OF THE PREFERRED EMBODIMENTS

Figure 1:
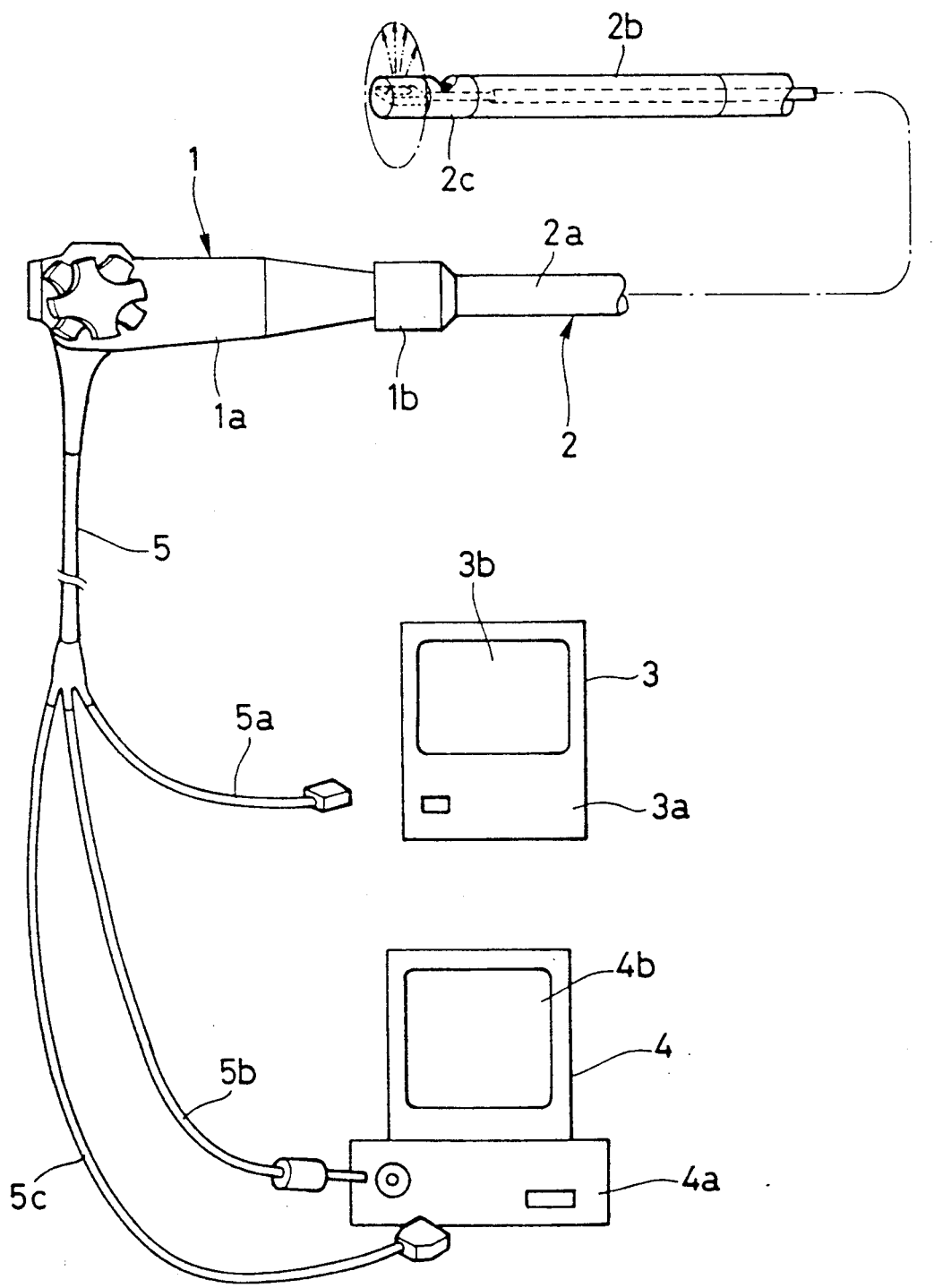

Now, the invention is described more particularly by way of the preferred embodiments shown in the drawings.

Although the ultrasonic internal examination system of the invention is described and shown by way of an ultrasonic endoscope in the following description and drawings, it is to be understood that the application of the invention is not restricted to ultrasonic endoscopes and includes other internal examination systems without the functions of the endoscope as long as they can provide a passage for insertion of the ultrasonic probe.

Referring to FIG. 1, indicated at 1 is an operating section and at 2 is an insert section of an ultrasonic endoscope to be inserted into an intracavitary portion of interest. The operating section 1 includes an endoscope operating portion 1a and an ultrasonic operating portion 1b. Except for a proximal end portion which is connected to the operating section 1, the insert section 2 is mostly constituted by a flexible portion 2a and has an angling portion 2b and a rigid tip portion 2c successively connected to the fore end of the flexible portion 2a. The operating section 1 is connected to an endoscopic observation terminal 3 and an ultrasonic observation terminal 4 through a cable harness 5. At branched ends, the cable harness 5 is provided with a light supply connector 3a to be connected to a light source of the endoscopic observation terminal 3, a power supply connector 5b to be connected to an image signal processor, and an ultrasonic connector 5c to be connected to the ultrasonic observation terminal 4.

Figure 2:
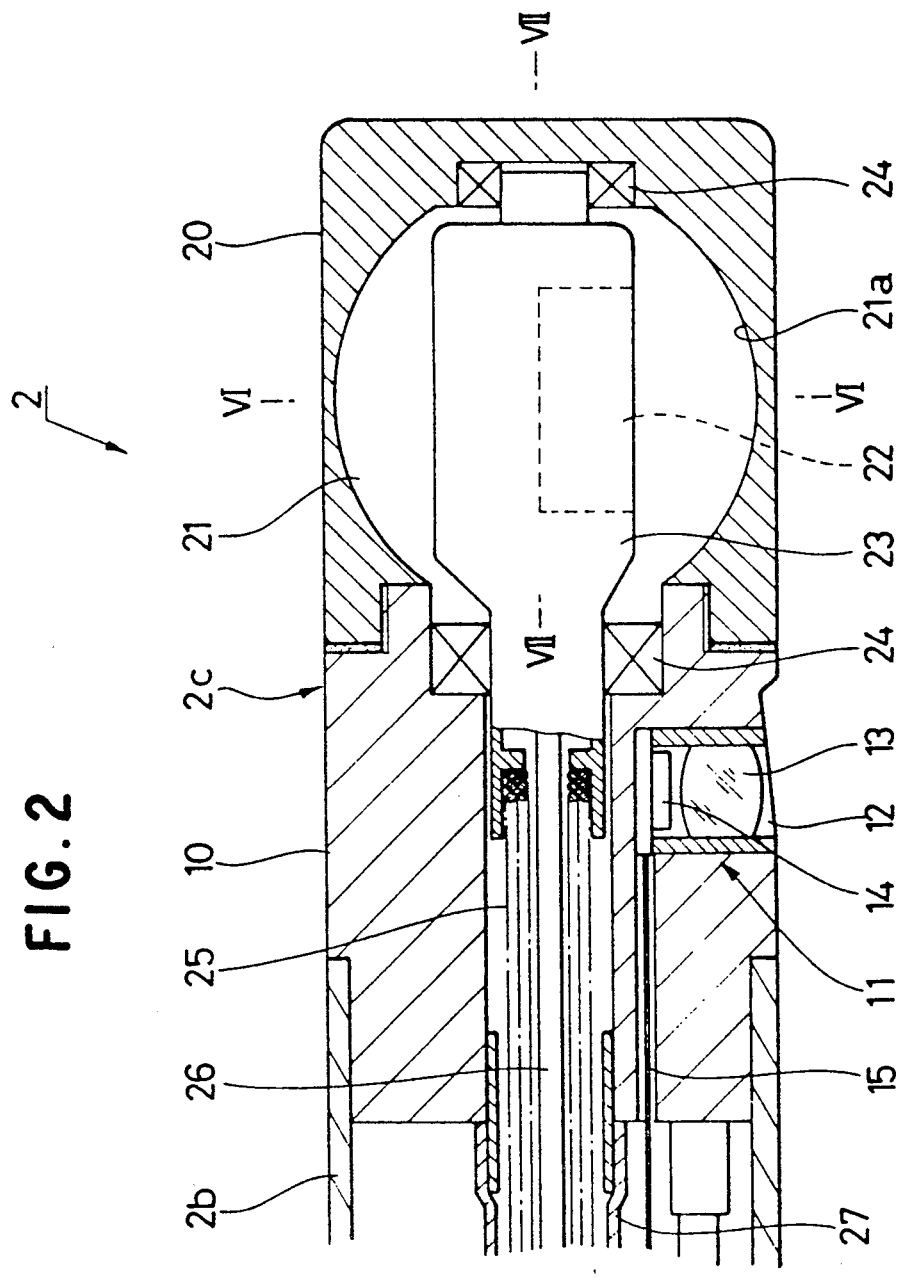

Illustrated in section in FIG. 2 is the rigid tip portion 2c of the insert section 2. As is clear therefrom, the rigid tip portion 2c is constituted by a main body 10 and a cap member 20 threaded on the fore end of the main body 10, accommodating an endoscopic image pick-up assembly 11 therein. The image pick-up assembly 11 is composed of an objective lens 13 fitted in an observation window 12, and a solid image sensor 14 located at the focal plane of the objective lens 13. A signal cable 15 is connected to the solid image sensor 14. In order to illuminate an internal portion to be examined, a light guide is passed through the insert section 2 and extended to an illumination window through which illuminating light is projected toward the internal portion of interest. These endoscope arrangements are known and thus omitted in the drawings.

On the other hand, an ultrasonic vibratory element 22 is accommodated in a cavity which is defined in the cap 20 and which is filled with an ultrasound transmissive medium such as deaerated water or the like. The ultrasonic vibratory element 22 is fitted in a support member 23 which is in turn rotatably supported in bearings 24. The support member 24 is connected to a control cable assembly 25 which has double or triple layers of coil springs around a signal cable 26. The signal cable 26 is connected at its fore end to the ultrasonic vibratory element 22. The control cable assembly 25 is sheathed in a flexible sleeve of a low friction material such as fluorine resin or the like, and led through the insert section 2 into the ultrasonic operating portion 1b of the operating section 1.

Figure 3:
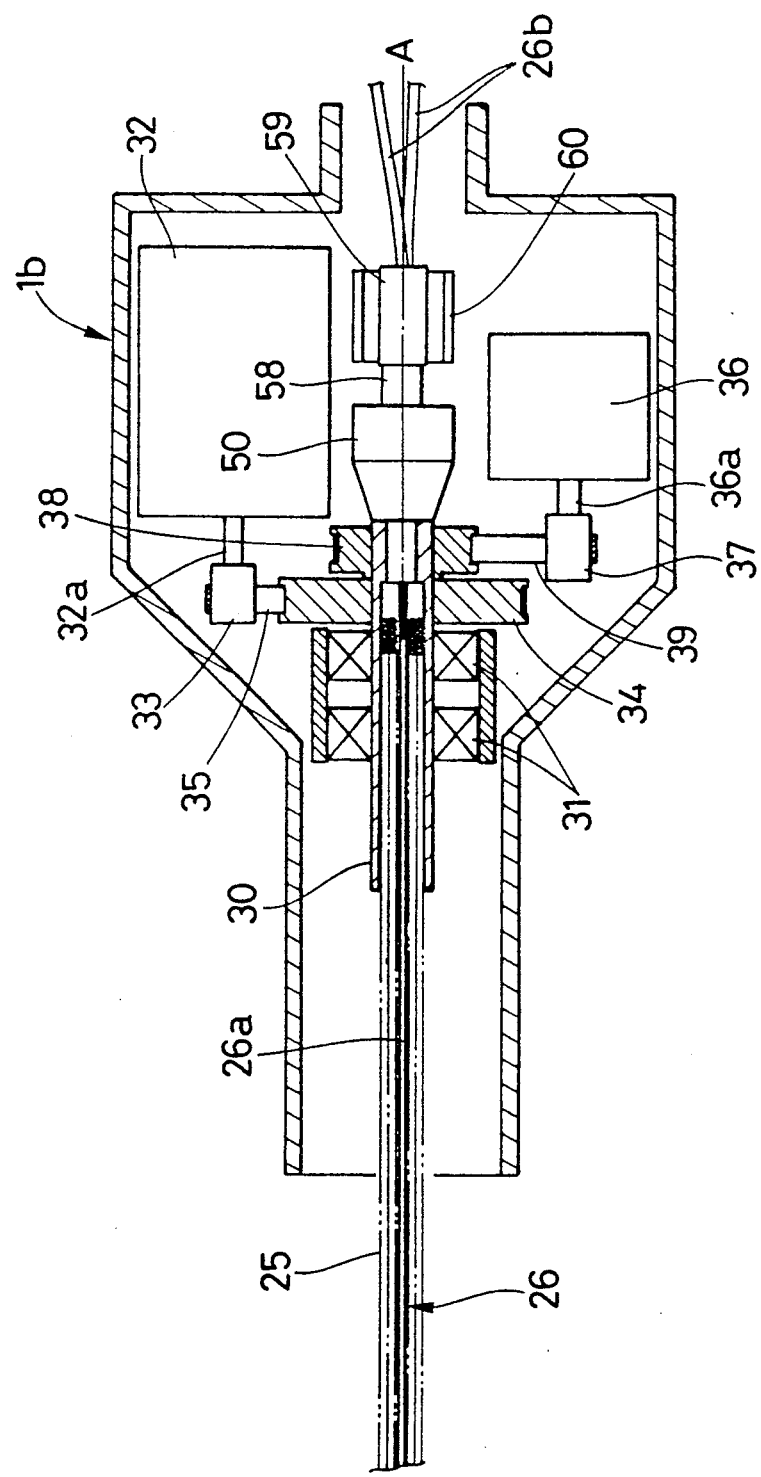
Figure 4:
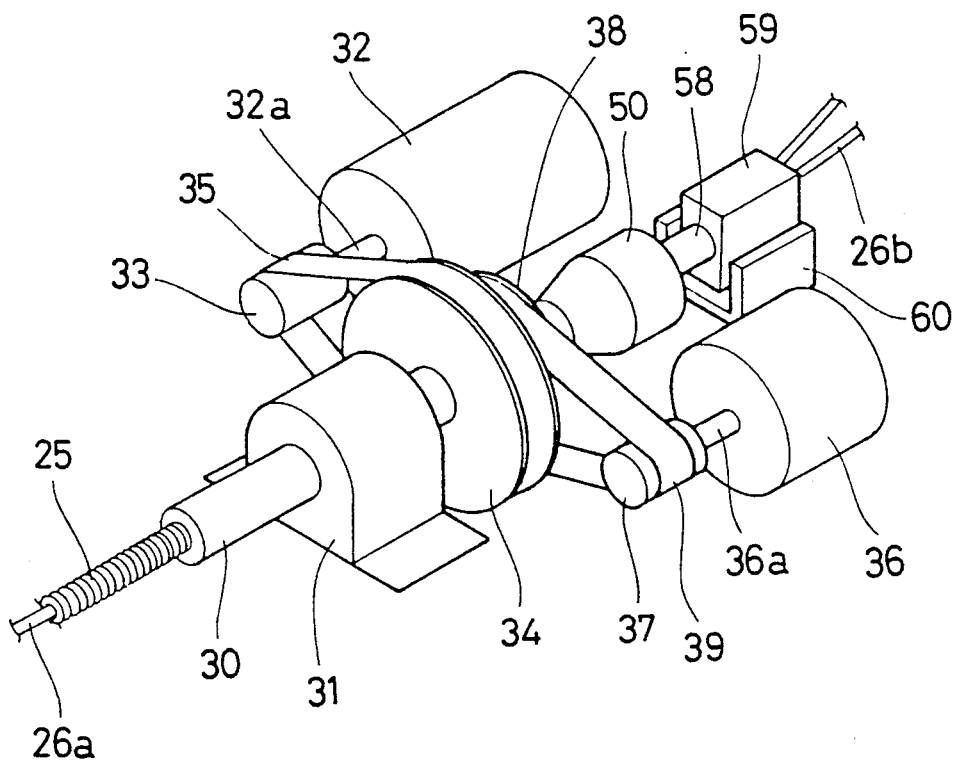
Figure 4:
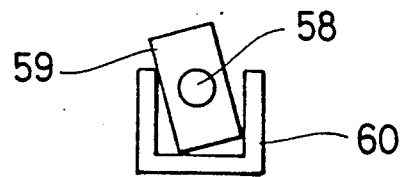

The ultrasonic operating portion 1b has the construction as shown in FIGS. 3 and 4. More specifically, as shown particularly in FIGS. 3 and 4(a), the distal end of the control cable 25, which is extended into the casing of the ultrasonic operating portion 1b, is securely connected to a rigid pipe 30 which is rotatably supported in a bearing 31. As a rotational drive means for rotating the control cable 25, the casing of the ultrasonic operating portion 1b houses therein a motor 32 which is coupled with the rigid pipe 30 through a transmission belt 35, which is passed around a pulley 33 mounted on the output shaft 32a of the motor 32 and a pulley 34 mounted on the rigid pipe 30. Consequently, as the motor 32 is actuated, the rigid pipe 30 is rotationally driven from the motor 32 to turn the ultrasonic vibratory element 22 through the control cable assembly 25 which is connected to the rigid pipe 30. In this instance, it is necessary to detect the rotational angle of the ultrasonic vibratory element 22 for the purpose of controlling the timing of ultrasonic pulse transmission and for determining the addresses of display positions of the return echo signals in the ultrasonic image. For these purposes, an encoder 36 is provided in the casing. The input shaft 36a of the encoder 36 is rotationally coupled with the rigid pipe 30 through a transmission belt 39 which is passed around a pulley 37 mounted on the input shaft 36a and a pulley mounted on the rigid pipe 30. As a consequence, as the rigid pipe 30 is rotated, this rotation is transmitted to the input shaft 36a of the encoder 36 through the transmission belt 39, permitting the encoder 36 to detect the rotational angle of the rigid pipe 30.

In this embodiment, the housed motor 32 and encoder 36 are located on the opposite sides of the rigid pipe 30 to accommodate these components and associated parts rationally in a compact form particularly in terms of compactness in axial length, as compared with a components arrangement in which the motor 32 and encoder 36 are located on the same side with regard to the rigid pipe 30. In addition, the transmission belts 35 and 39, which transmit rotation from the motor 32 to the rigid pipe 30 and from the rigid pipe 30 to the encoder 36, need to be maintained in a tensioned state to a certain degree. In this regard, the location of the motor 32 and encoder 36 on the opposite sides of the rigid pipe 30 has the merit of balancing the tensions of the two transmission belts with each other, precluding overloading damages to the bearing 31 which rotatably supports the rigid pipe 30.

The signal cable 26 which provides power supply and signal transfer between the ultrasonic vibratory element 22 and the ultrasonic image observation terminal 3 is divided into a fore cable portion 26a which is connected to the ultrasonic vibratory element 22, and a rear cable portion 26b which is connected to the ultrasonic image observation terminal 3. Inserted between the fore and rear cable portions 26a and 26b is a rotary connector 50 which permits the fore cable portion 26a to rotate with the ultrasonic vibratory element 22 while holding the rear cable portion 26b in fixed state in a the rotational direction.

Figure 5:
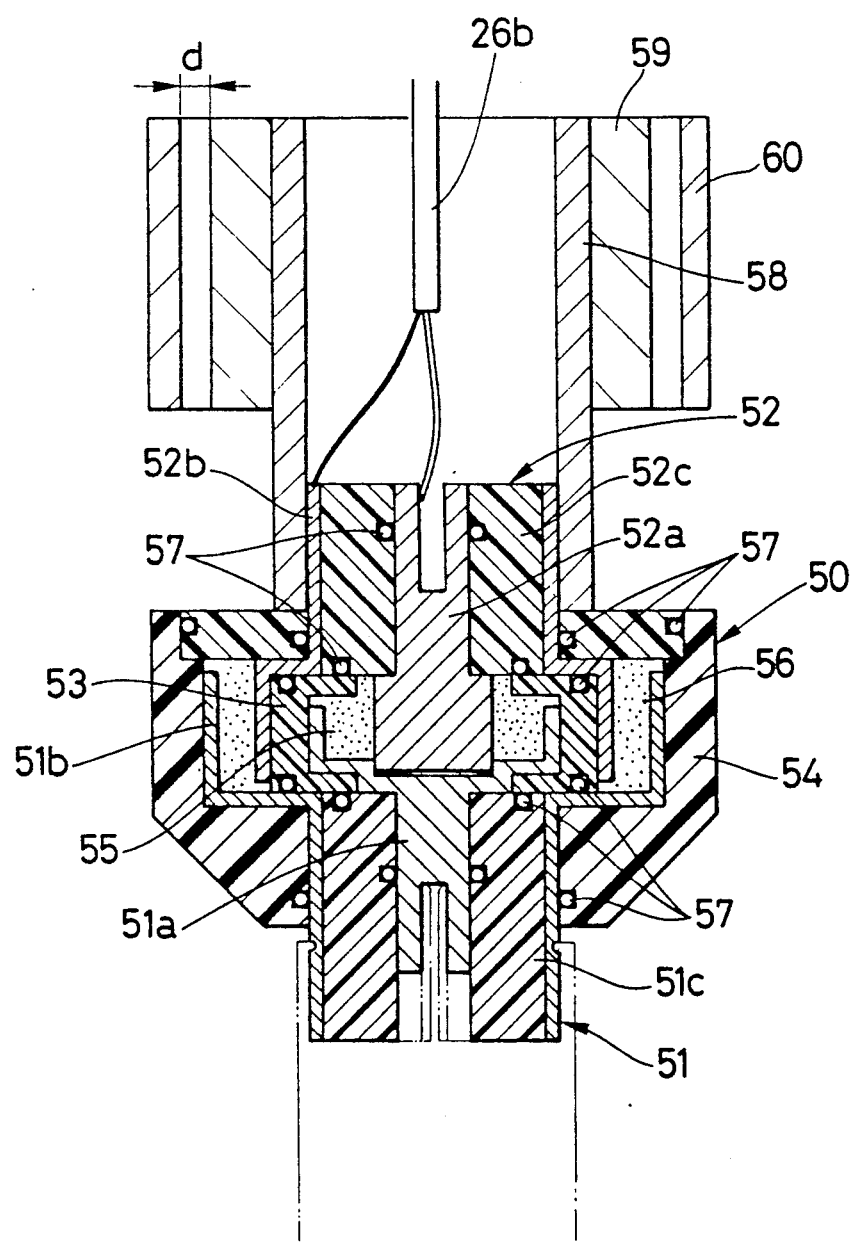

As illustrated in FIG. 5, the rotary connector 50 is largely composed of a rotatable coupling member 51 which is connected to the rotatable fore cable portion 26a, and a fixed coupling member 52 which is connected to the nonrotatable rear cable portion 26b. The rotatable coupling member 51 is provided with a pair of inner and outer electrodes 51a and 51b, and an insulating member 51c which is interposed between the inner and outer electrodes 51a and 51b. On the other hand, the fixed coupling member 52 is provided with an inner electrode 52a which is loosely fitted in the inner electrode 51a of the rotatable coupling member 51, an outer electrode 52b which is loosely fitted in the outer electrode 51b, and an insulating member 52c which is interposed between the inner and outer electrodes 52a and 52b. Further, insulators 53 and 54 are interposed between the inner electrode 51a of the rotatable coupling member 51 and the outer electrode 52b of the fixed coupling member 52, and around the outer periphery of the outer electrode 51b of the rotatable coupling member 51, respectively. The space between the inner electrodes 51a and 52a and the space between the outer electrodes 51b and 52b of the two coupling members are filled with fluid contacts 55 and 56 of mercury or other conductive fluid. Further, in order to prevent leaks of the fluid contacts 55 and 56, seal members 57 like O-rings are fitted in necessary places. Cable portions 26a and 26b which constitute the cable 26 are in the form of coaxial cables having core conductors connected to the inner electrodes 51a and 52a and the outer conductors connected to the outer electrodes 51b and 52b, respectively.

The rotatable coupling member 51 needs to be rotated with the rigid pipe 30 when the latter is rotationally driven from the motor 36. For this purpose, an end portion of the rotatable coupling member 51 is fixedly connected to the rigid pipe 30 for integral rotation therewith. While the rotatable coupling member 51 of the rotary connector 50 is rotated with the rigid pipe 30, the fixed coupling member 52 has to be retained in a non-rotating state. However, complete fixation of the fixed coupling member 52 might hinder smooth rotation of the rotatable coupling member 51. Therefore, a sleeve 58 with an insulating property is extended onto the fixed coupling member 52, and a rectangular block 59 which is fixed on the rear end of the sleeve 52 is nested in a rotation delimiting member 60 of substantially U-shape in section, leaving clearances of width d therebetween. As seen in FIG. 4(b), the rectangular block 59 is movable in an arbitrary direction within a delimited range as determined by the clearance width d. Consequently, the axis A (see FIG. 3) between the bearing 31 and the rotary connector 50 is rockable within a predetermined range to absorb deflections of the axis A between the rigid pipe 30 and rotary connector 50 by the clearances between the rectangular block 59 and rotation delimiting member 60.

With the ultrasonic internal examination system as arranged above, the insert section 2 is introduced into an intracavitary portion, locating the ultrasound vibratory element 22 on the rigid tip portion 2c at an intracavitary wall portion to be examined, and, while rotating the ultrasonic vibratory element 22 for a radial scan, ultrasonic pulses are transmitted into the intracavitary wall portion from the ultrasonic vibratory element 22, and return echo signals received by the vibratory member 22 from various depths of the wall are sent to the ultrasonic image observation terminal 4 to undergo a predetermined signal processing thereby to produce an ultrasonic image of a cross-sectional area of the intracavitary wall tissues under examination.

In order to enhance the resolution of the ultrasonic image, as mentioned hereinbefore, the ultrasonic beam to be directed from the ultrasonic vibratory member 22 needs to be converged to a certain depth of the intracavitary wall under examination. For this purpose, the ultrasonic transmissive medium which is sealed in the cavity 21 is adapted to constitute an acoustic lens.

More specifically, the cavity 21 of the cap 20 is provided with, on and around its inner periphery, a curved wall portion 21a which is concaved toward the radial direction substantially with the same radius of curvature as the circumference of the girder of the cylindrical cap 20. Therefore, as shown particularly in FIGS. 6 and 7, the ultrasonic transmissive medium in the cap 20 presents arcs of substantially the same radius of curvature both in the cross section across the axis of the cap 20, namely, in the scanning direction and in the longitudinal section perpendicular to the scanning direction, thus presenting a spherical surface configuration as a whole. Accordingly, due to the difference in acoustic impedance of the ultrasonic transmissive medium in the cavity 21 from the cap 20 and the intracavitary wall portion under examination, the spherical surface of the ultrasonic transmissive medium functions as an acoustic lens to converge the ultrasonic beam into an extremely narrow spot to the same degree both in the direction of cross-section of the cap or scanning direction and in the direction of the longitudinal section perpendicular to the scanning direction.

Figure 8:
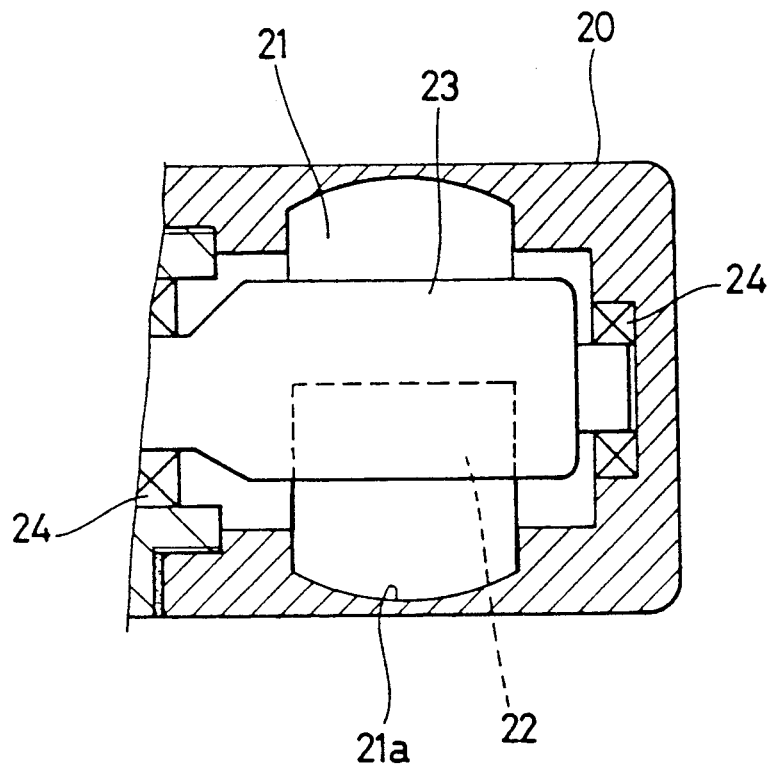
FIG. 8 is a schematic sectional view of a tip portion of the insert cable in a second preferred embodiment of the invention.

In this instance, the curved wall portion 21a on the inner wall surface of the cavity 21 is not necessarily required to be formed completely around the inner periphery of the cap 20, and may be provided only in a particular region which is intended for transmission and reception of ultrasonic signals, as shown in FIG. 8. This arrangement contributes to reduce noises by preventing scattering components of the transmitted ultrasonic energy from entering the effective beam region. Further, provision of coarsened surfaces on the non-curved inner wall portions can attenuate the scattering components of the transmitted ultrasonic energy through irregular reflection. Such scattering components can be removed almost completely by bonding thereon an acoustic material such as rubber admixed with metallic micro powder.

The curved wall portion 21a on the inner wall surface of the cavity 21 is formed substantially with the same radius of curvature as the circumference of the cylindrical cap 20 in the foregoing embodiments. However, they may be formed to have different radii of curvature in a case there is necessity for setting the radial and axial sound fields in a certain given ratio. Besides, in addition to the setting of the radial and axial sound fields, the longitudinal and transverse dimensions of the ultrasonic vibratory member may be varied to secure a desired beam pattern.

Obviously, numerous modifications and variations and the present invention are possible in light of the above teachings. It is therefore to be understood that within the scope of the appended claims, the invention may be practiced otherwise than as specifically described herein.

What is claimed is:

1. An ultrasonic internal examination apparatus, which comprises:

a probe having an insert section with a rigid tip portion at a distal end thereof for being inserted into an intracavitary portion of interest, said tip portion having a substantially spherically shaped cavity and a substantially cylindrical outer profile such that said insert section has a substantially uniform diameter over the length thereof;

an ultrasonic vibratory element positioned in said cavity; and an ultrasonic transmissive medium of a predetermined acoustic impedance located in said cavity for transmission and reception of ultrasonic signals and for forming an acoustic lens wherein said cavity has an inner wall surface of a substantially circular shape along an axial cross-section thereof for focusing of said ultrasonic signals transmitted from said vibratory element.

2. The ultrasonic internal examination apparatus as defined in claim 1, which comprises means for acoustically masking at least a portion of wall surfaces on the inner periphery of said rigid tip portion.

* * * * *